United States Patent [19]

Puletti et al.

[11] Patent Number: 4,718,898
[45] Date of Patent: Jan. 12, 1988

[54] HOT MELT ADHESIVE WASTE BARRIER

[75] Inventors: Paul P. Puletti; Stanley J. Decowski, Jr., both of Glen Gardner, N.J.

[73] Assignee: National Starch and Chemical Corporation, Bridgewater, N.J.

[21] Appl. No.: 878,907

[22] Filed: Jun. 26, 1986

Related U.S. Application Data

[62] Division of Ser. No. 719,196, Apr. 3, 1985, Pat. No. 4,627,847.

[51] Int. Cl.$^4$ ............................................. A61F 13/16
[52] U.S. Cl. .................................................. 604/366
[58] Field of Search ............... 604/358, 366, 370, 371, 604/374, 375

[56] References Cited

U.S. PATENT DOCUMENTS

| 3,520,303 | 7/1970 | Endres . |
| 3,672,371 | 6/1972 | Roeder . |
| 3,683,916 | 8/1972 | Mesek et al. . |
| 3,693,622 | 9/1972 | Jones, Sr. . |
| 3,799,167 | 3/1974 | Miller et al. . |
| 4,075,382 | 2/1978 | Chapman et al. ................... 428/192 |
| 4,112,153 | 9/1978 | Butterworth et al. .............. 427/390 |
| 4,136,699 | 1/1979 | Collins et al. . |
| 4,287,251 | 9/1981 | King et al. ........................... 428/198 |
| 4,392,862 | 7/1983 | Marsan et al. ...................... 604/366 |
| 4,392,908 | 7/1983 | Dehnel ................................. 427/194 |
| 4,397,645 | 8/1983 | Buell ................................... 604/380 |
| 4,460,364 | 7/1984 | Chen et al. .......................... 604/387 |
| 4,503,098 | 3/1985 | Potts .................................... 427/394 |

FOREIGN PATENT DOCUMENTS

| 496255 | 4/1977 | Australia . |
| 1182601 | 2/1985 | Canada . |
| 0091412 | 10/1983 | European Pat. Off. . |

Primary Examiner—John D. Yasko
Attorney, Agent, or Firm—Ellen T. Dec; Edwin M. Szala

[57] ABSTRACT

Leakage resistant waste barriers for use on absorbent articles are prepared by coating a portion of a nonwoven sheet with a water insoluble or water impermeable hot melt adhesive composition.

3 Claims, 4 Drawing Figures

HOT MELT ADHESIVE WASTE BARRIER

This application is a division of application Ser. No. 719,196, filed Apr. 3, 1985, now U.S. Pat. No. 4,627,847.

BACKGROUND OF THE INVENTION

This invention relates to nonwoven waste barriers having adhesive properties and to absorbent articles prepared therewith. In particular, the invention relates to waste barriers for use in disposable absorbent articles such as diapers, sanitary napkins, bed pads, incontinent pads, and the like.

Conventional disposable absorbent articles generally comprise an absorbent pad positioned between a fluid permeable nonwoven topsheet and a fluid impermeable backsheet. The nonwoven topsheet draws the waste away from the contacting skin and into the absorbent batting while the fluid impermeable backsheet prevents the absorbed fluids from leaking out of the absorbent article. Numerous variations of, and elements in addition to, these basic components have been taught with each variation or additional element being directed to improving a specific characteristics of the article. Regardless of the particular construction, however, it is expected that the absorbent article will have characteristics which permit liquid to rapidly penetrate the liquid permeable topsheet while large quantities of liquid are absorbed by the core. Once in contact with the absorbent core, the liquid will tend to migrate or spread away from the source of discharge, thereby migrating throughout the thickness of and toward the perimeter of the absorbent core. The liquid which penetrates the thickness of the core will be prevented from wetting the vicinity surrounding the diaper by the liquid impermeable backsheet; however, the problem remains of preventing escape or leakage of liquid which migrates toward the perimeter of the absorbent article.

Providing a barrier to reduce or eliminate the amount of leakage from the perimeter of these disposable articles has become a primary concern for the manufacturers. In attempting to solve this problem the manufacturer has to consider the effects of the proposed barriers on other requirements for the article. In particular, it is essential that the barrier not reduce the absorbency of the core; it must not affect the softness or "hand" of the non-woven topsheet; no irritating compounds can be used since the uses generally contemplate contact with the skin; the barrier must be economical and, importantly, it must not reduce line speeds during production of the absorbent articles.

Prior methods to provide such barriers have been deficient in at least one of these areas. Thus, U.S. Pat. No. 3,520,303; 4,397,645 and Canadian Pat. No. 1,182,601 teach the insertion of a separate barrier film or other barrier construction, positioned between the topsheet and the backsheet and partially overlapping the absorbent core. Such barriers are difficult to handle in the high speed equipment and generally require two separate adhesive applications in order to affix them or require the use of heat seal equipment which may weaken the integrity of the fluid impermeable backsheet. U.S. Pat. Nos. 3,693,622 and 3,799,167 teach the use of liquid repellant compositions on either the absorbent core or nonwoven portion of the article. This approach requires the use of the fluid repellant in the form of liquid solutions which effectively saturate the surface to which they are applied. Thus, if applied to the absorbent core, the solution will substantially reduce the absorbency of the subsequent product, while if applied to the nonwoven topsheet it will completely penetrate the sheet thereby reducing the softness or feel of the nonwoven sheet which will then cause discomfort to the wearer. Furthermore, these solutions require drying or curing to effect the fluid repellency treatment, steps which substantially reduce the speeds at which the disposable articles are manufactured. For example, the U.S. Pat. No. 3,799,167 requires curing times of 15 seconds to 5 minutes; a curing time which clearly could not be tolerated in conventional diaper manufacturing equipment which produce diapers at a rate of 4 to 15 per second.

SUMMARY OF THE INVENTION

We have now found that a self-adhesive, leakage-resistant, waste barrier may be provided by coating a portion of the nonwoven topshet with a hot melt adhesive to deposit a liquid impermeable film thereon. Thus, in its broadest embodiment, the present invention contemplates a disposable absorbent article comprising an absorbent core at least one surface of which is in contact with a nonwoven sheeting, said sheeting containing thereon an appropriately positioned leakage resistant waste barrier formed by coating a portion of the nonwoven with a hot melt adhesive. In a narrower embodiment, the present invention contemplates a disposable absorbent article comprising an absorbent core encased in an outer covering layer having a liquid permeable nonwoven topsheet and a liquid impermeable backsheet portion, the disposable article being provided with at least one leakage resistant waste barrier formed by coating at least a portion of the nonwoven topsheet with a hot melt adhesive.

The precise positioning of the waste barrier will vary depending upon the particular disposable construction being manufactured. Thus, in the case of disposable diapers, the waste barrier may be positioned at the end seal of the diaper with a portion of the barrier overlaying the lateral end portions of the absorbent core so as to prevent leakage to the waist and chest area of the baby or incontinent adult. A similar end seal/waste barrier construction can be employed for a sanitary napkin to prevent lateral leakage of the menstrual fluid.

In the case of sanitary napkins and disposable bed pads, it is also contemplated that the entire portion of the nonwoven which is intended to cover the bottom of the absorbent core (i.e., that portion which will not be in contact with the body) be coated with the hot melt adhesive so as to form a complete barrier which will totally replace the conventionally employed fluid impermeable film. Depending upon the side of the nonwoven coated, the hot melt adhesive will perform different functions in addition to serving as a waste barrier. Thus, if coated on the side of the nonwoven which will not come into direct contact with the absorbent core, the hot melt if formulated to be pressure sensitive could be utilized as a positioning adhesive as required in "beltless" pad constructions. Alternatively, if coated on the side of the nonwoven which will directly contact the core, the hot melt adhesive coating would not only serve as a waste barrier but could also aid in construction and/or serve to position any super-absorbent powders or films used, the migration of which is presently difficult to prevent using conventional techniques.

Finally, in the case of bed pads, it is also contemplated that the hot melt adhesive coating be used to form a waste barrier around the total perimeter of the pad.

It will be recognized that for all the above contemplated uses, the hot melt adhesive serves a dual function of securing as well as of preventing leakage from the core, thus requiring no reduction in manufacturing line speeds. Further, since the hot melt is not a saturant but rather a coating, it does not require further curing or drying and can be applied only to the interior surface of the nonwoven which does not come in contact with the skin so as to provide no reduction in softness or feel of the article.

BRIEF DESCRIPTION OF THE DRAWINGS

Two of the general embodiments of the invention are illustrated by the attached figures. These drawings are merely illustrative of certain embodiments of the invention but are not considered as limiting or essential to an understanding thereof.

FIG. 2A represents an elevational perspective view of an unassembled sanitary napkin construction of the prior art utilizing the film barrier while

DETAILED DESCRIPTION OF THE PREFERRED EMBODIMENTS

Figure 1A:
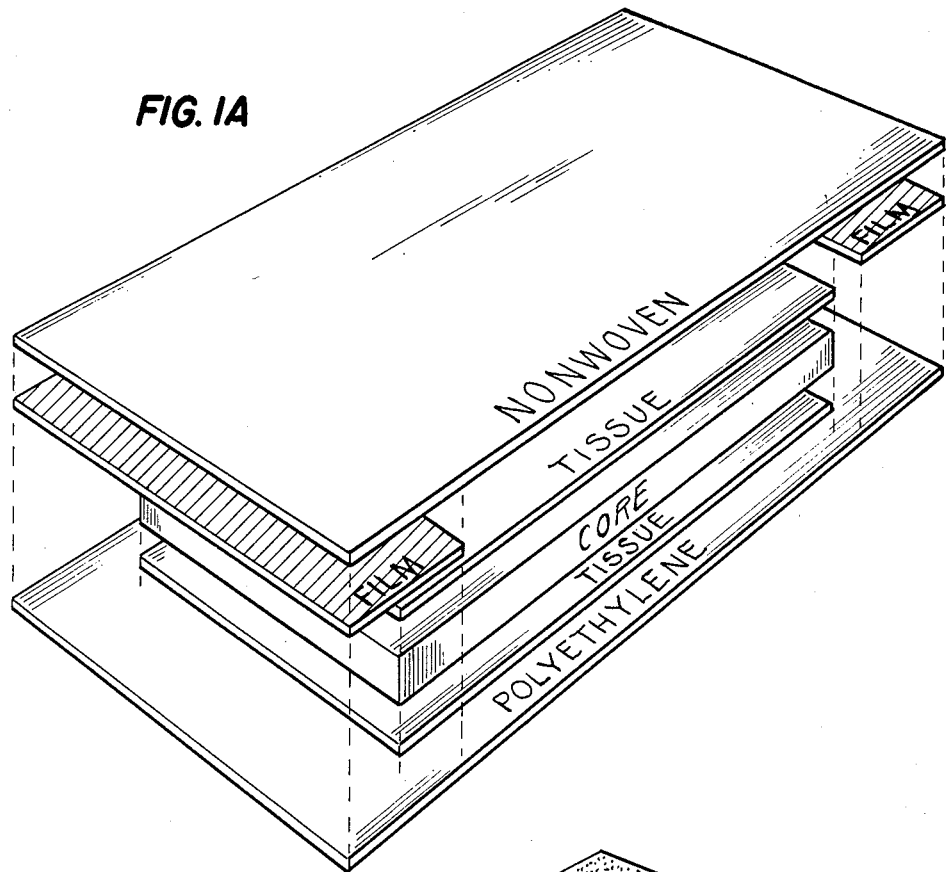
FIG. 1A represents an elevational perspective view of an unassembled conventional disposable diaper construction of the prior art utilizing a separate film waste barrier, the barrier being represented by the hatched portion of the figure.

Hot melt adhesives are 100% solid materials and do not contain nor require any solvents. They are solid materials at room temperature but, on application of heat, melt to a liquid or fluid state in which form they are applied to a substrate. On cooling, the adhesive regains its solid form and gains its cohesive strength. In this regard, hot melt adhesives differ from other types of adhesives which achieve the solid state through evaporation or removal of solvents, or by polymerization.

Virtually any water insoluble or water impermeable hot melt adhesive composition will serve the waste barrier function contemplated herein. For convenience, it is generally preferred to employ one of the hot melt adhesives already being utilized by the manufacturer in the construction of the particular absorbent article. Representative of suitable adhesives are those hot melt adhesive compositions based on ethylene/vinyl acetate copolymers, isotactic or atactic polypropylene, styrene-butadiene, styrene-isoprene, or styrene-ethylene-butylene A-B-A or A-B-A-B block copolymers such as those sold under the Kraton, Solprene and Stereon tradenames; or mixtures thereof. In addition to the base polymer, these hot melt adhesive compositions generally contain tackifiers, oils and/or waxes as well as conventional additives including stabilizers, anti-oxidants, pigments and the like. Typical of such formulations are those described in U.S. Pat. Nos. 4,460,728; 3,492,372; 4,411,954; 4,419,494; 4,136,699; 4,259,200 etc.; the disclosures of which are incorporated herein by reference.

The hot melt adhesive may be applied to the nonwoven sheeting using any conventional methods such as slot coating, transfer coating, spray coating or nozzle wheel applicator. The hot melt adhesive is generally coated so as to form a continuous film at least 1.0 mils in thickness, generally at least 1.2 mils in thickness and preferably at least 3 mils in thickness, and in such a manner as to insure that virtually no pin holes exist in the overall coated film. The entire coating may be applied in one application or two or more adhesive applications may be used to achieve the desired thickness. Alternatively, that portion of the nonwoven to be utilized as the waste barrier may be first coated with a thin application of a low molecular weight thermoplastic such as a low molecular weight polyethylene or ethylene vinyl acetate copolymer and subsequently coated with a layer of the hot melt adhesive. In accordance with the latter embodiment, the lower molecular weight (and less expensive) coating will provide some waste barrier properties but the final coating with the hot melt adhesive will be required to provide additional barrier properties as well as sealant properties to the construction.

In the case of disposable diapers or sanitary napkins utilizing the waste barrier at the peripheral ends thereof, the adhesive is conveniently metered laterally onto the continuous nonwoven topsheet at timed intervals so as to position the coated portions to fall between the spaced absorbent core sections as they are transported on the conveyorized manufacturing equipment. The amount of adhesive is metered so as to form a coating twice as long as needed. By so doing, when the continuously produced products are cut in half traversely to form and seal the diaper or napkin, one half of the coating provides the adhesive for the barrier and seal of the trailing edge of the lead diaper while the other half provides the barrier and seal for the leading edge of the following diaper or napkin.

Figure 1B:
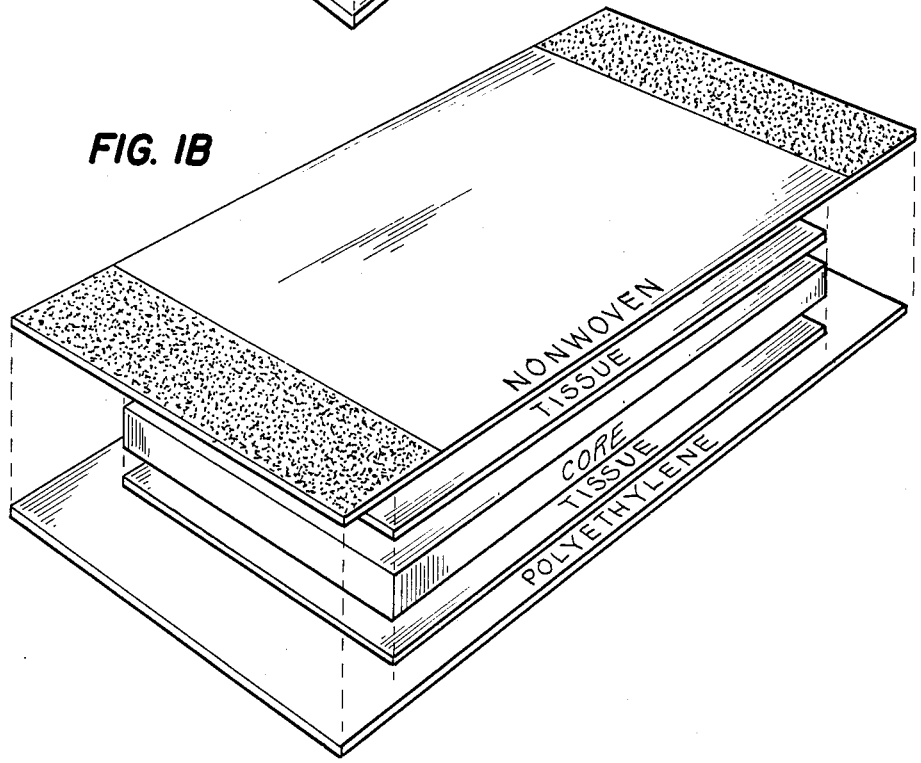
FIG. 1B represents a similar construction utilizing the adhesive barrier of the present invention, as shown by the stippled portion of the nonwoven topsheet.

In this embodiment as shown in FIG. 1B, the stippling represnts the coated hot melt adhesive. In this figure it is seen that the nonwoven topsheet and fluid impermeable backsheet are coterminus, while the absorbent core, preferably surrounded by tissue for integrity, is slightly smaller in overall dimension. The hot melt coating thus forms the end seal portion joining the top and back sheets so as to encase the absorbent core while additionally covering a portion of the absorbent core thereby forming the desired barrier. As a general guide to the extent of the overlapping required to form an adequate waste barrier, it is suggested that the width of the overlap of the core be approximately the same width as the end seal itself.

Figure 2A:
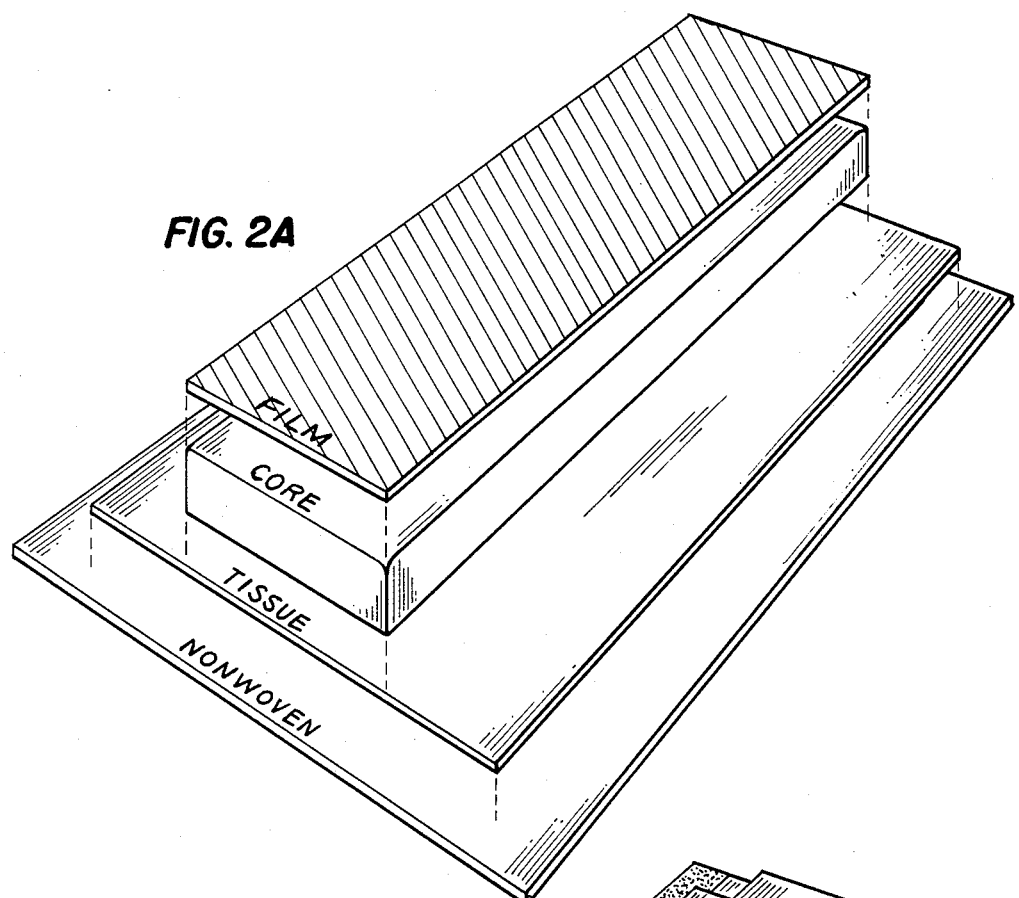
Figure 2B:
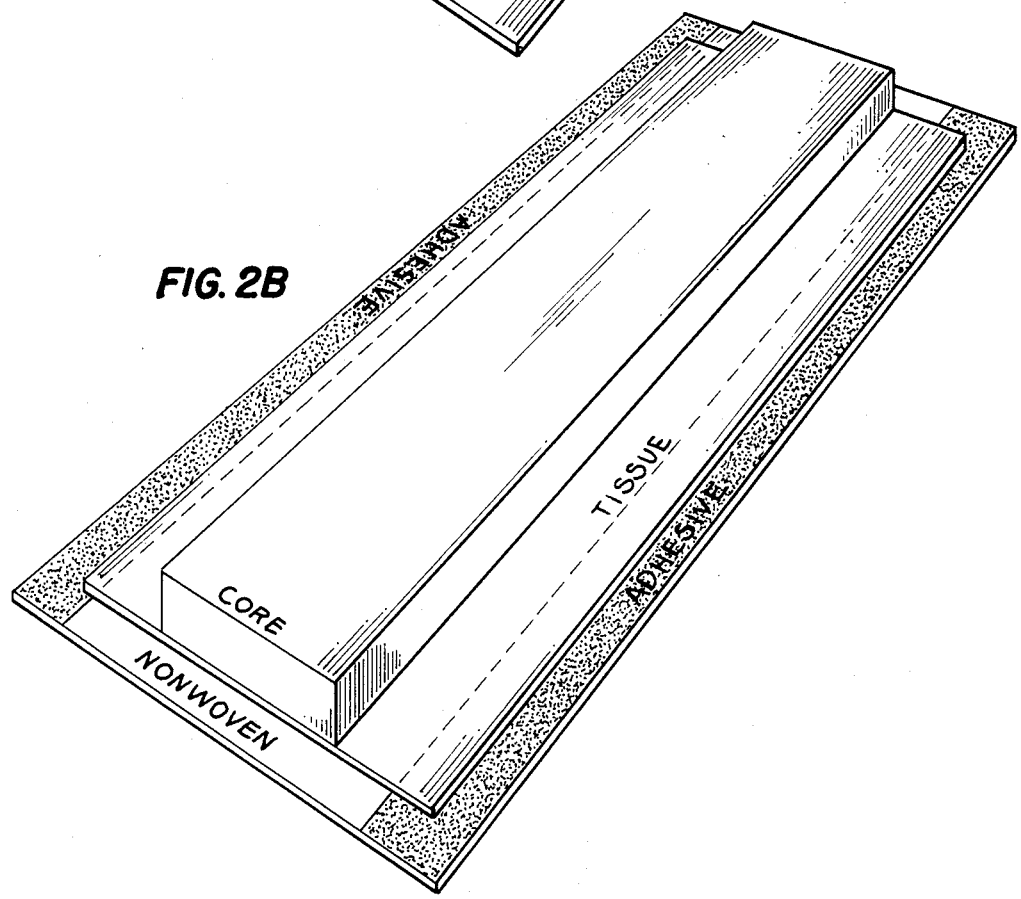
FIG. 2B represents a similar sanitary napkin utilizing the hot melt adhesive coated nonwoven waste barrier of the invention. Again, the shaded portion represnts the film of the prior art while the hatched portion shows the portion of the nonwoven which is coated in accordance with the present invention.

In the case of waste barriers which are to cover the entire bottom surface of the absorbent core, as illustrated in FIG. 2B, the nonwoven sheet is coated with the adhesive at appropriate widths along the continuous longitudinal edge(s). While only one such edges may be coated and the core then positioned so that the bottom portion thereof will be completely covered with the coated nonwoven, it is generally preferred to coat both edges as shown in FIG. 2B and then position the absorbent core substantially in the center of the thus coated nonwoven, which when overlapped and joined will form the waste barrier. This latter construction is especially preferred when it is desired to coat the bottom of the core with super-absorbent powders or films which are known to substantially increase the absorbency of the pads but which, to date, are known to migrate away from the areas in which they are desired.

The particular materials used in the manufacture of the absorbent article are not critical and will vary depending upon the particular construction as well as the manufacturer. In general, the nonwoven topsheet or cover sheet will consist of any fluid permeable, compliant material containing hydrophilic or hydrophobic components. Nonwoven webs comprising natural or synthetic fibers or mixtures thereof are generally used although some constructions may employ thread-reinforced nonwoven webs or cellulose wadding. There are a number of manufacturing techniques which may be utilized to prepared such topsheets. For example, the web may be dry or wet laid utilizing carding, air-laying or spunbonding techniques to produce the web which is then joined mechanically, chemically or thermally. Preferable topsheets for use in the articles contemplated herein have a basis weight range of from about 18 to about 30 grams per square yard, a minimum wet tensile strength of at least 400 grams per cm. in the machine direction and at least about 55 grams per cm. in the crossmachine direction. Examples of suitable topsheets are described in U.S. Pat. No. Re. 26,151 which utilizes a hydrophobic nonwoven rayon web bonded with a thermoplastic binder. Other suitable topsheets are shown in U.S. Pat. No. 3,860,003 which describes a spunbonded nonwoven polyester fabric, in particular a fibrous topsheet comprising by weight about 65 percent staple length polyester fibers having a denier of about 1.5, such as Kodel Type 411 polyester fiber marketed by Tennessee Eastman Corporation, about 15 percent staple length (i.e., at least 0.625 in.) crimped rayon fibers having a denier of approximately 1.5; and about 20 percent acrylic copolymer binder such as Celanese CPE 8335 marketed by Celanese Corporation. Other nonwoven topsheets may comprise thermally bonded webs of thermoplastic fibers such as polypropylene or may be a blend of a higher melting matrix fiber such as rayon, cotton or polyester with a lower melting binder fiber. Typical of this latter class of nonwovens are those described in U.S. Pat. No. 4,315,965.

The absorbent core is typically a highly porous, loosely compacted batting such as formed from a layer of cellulosic fluff from wood pulp, multiple layers of cellulose wadding, absorbent cotton or rayon fibers, or any similar material with suitable absorbent properties.

It is optional, although preferred, to cover or encase the absorbent core in a tissue so as to provide more integrity to the core durmanufacturing operations and afterwards to reduce the tendency of the absorbent core to lump or ball when wetted. The tissue layer may comprise densified compacted cellulosic fibers of relatively high wettability and relatively high fluid retentivity such as described in U.S. Pat. No. 3,017,304.

The fluid impermeable backsheet may be of polyethylene or other thin, pliable, plastic film such as polypropylene or ethylene and polypropylene copolymers with acrylate or vinyl acetate. The backing sheet may be treated so as to be vapor permeable as described in U.S. Pat. No. 4,341,216.

A typical diaper containing the waste barrier of the invention may be constructed in accordance with conventional manufacturing techniques, e.g., utilizing end-seal or multi-line type constructions and may be rectangular or hour-glass in shape. The longitudinal edges may be partially or completely elasticized. They may further have adhesive tabs applied to one end for fastening purposes or pins may be used. Similarly, the invention may be adapted to use on any of the wide variety of sanitary napkin constructions and shapes and may be used in the production of maxi-pad, mini-pad or pantiliner type absorbent articles.

In order to illustrate the efficacy of the hot melt waste barriers of the present invention, a conventionally employed disposable construction hot melt adhesive based on 25% Stereon 840 (a styrene-butadiene rubbery copolymer available from Firestone), 60% Zonatoc 105 (an aromatic terpene tackifier), and 15% white mineral oil was coated onto a nonwoven fabric and then placed between two plastic sleeves which were clamped together. Water was poured into the top sleeve and the apparatus observed for any liquid leakage from the bottom sleeve. The tests were terminated when leakage was observed or after twenty-four hours if no leakage appeared. After 24 hours, no leakage was observed from samples coated at adhesive levels of 3 mils in thickness, thereby showing the high efficacy of the adhesive coated nonwoven as a waste barrier. Another series of samples were tested coating the nonwoven two times, each with an 0.6 mil thicknesses of the adhesive to form a coating 1.2 mils in total. No leakage was observed.

Additional tests were run by coating the nonwoven first with a 1 mil thickness of Ultrathene UE 80271, a low molecular weight ethylene/vinyl acetate copolymer, and then with a second coating using the hot melt adhesive described above. When second coatings were made at thicknesses of 0.5, 1.0 and 1.5 mils, none of the coated samples exhibited leakage during the entire test period.

Further, other Stereon type hot melt adhesives as well as those adhesive compositions based on ethylene/-vinyl acetate copolymers, Kraton-type A-B-A block copolymers and atactic or isotactic polypropylene have been observed to exhibit similar waste barrier properties as required herein.

Now that the preferred embodiments of the present invention have been described, many modifications and variations will become readily apparent in constructing the waste barriers of the present invention. Hence the invention has been described in detail above for purposes of illustration only and is not intended to be limited by this description or otherwise to exclude any variation or equivalent that would be apparent from, or reasonably suggested by, the foregoing disclosure to the skill of the art.

We claim:

1. A sanitary napkin comprising an absorbent core encased in an outer layer wherein the outer layer comprises a liquid permeable nonwoven topsheet and a liquid impermeable backsheet portion; the napkin being provided with a leakage resistant waste barrier formed by coating a water insoluble or water impermeable hot melt adhesive onto the lateral end portions of the surface of the nonwoven topsheet which is in contact with the core, the barrier extending over a portion of the lateral end of the absorbent core.

2. A sanitary napkin comprising an absorbent core encased in a liquid permeable nonwoven sheeting, wherein substantially the entire surface of the nonwoven sheeting which is in direct contact with the bottom surface of the absorbent core is coated with a water insoluble or water impermeable hot melt adhesive thereby providing a leakage resistant barrier.

3. The sanitary napkin of claim 2 wherein there is additionally coated on the hot melt adhesive, a superabsorbent powder or film.

* * * * *